United States Patent [19]
Berg et al.

[11] Patent Number: 6,165,489
[45] Date of Patent: *Dec. 26, 2000

[54] CROSSLINKED COLLAGEN COMPOSITIONS FOR IN SITU ADMINISTRATION

[75] Inventors: Richard A. Berg, Los Altos; Joel S. Rosenblatt; Woonza M. Rhee, both of Palo Alto, all of Calif.

[73] Assignee: Cohesion Technologies, Inc., Palo Alto, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 09/300,889

[22] Filed: Apr. 28, 1999

Related U.S. Application Data

[63] Continuation of application No. 08/730,157, Oct. 15, 1996, abandoned, which is a continuation of application No. 08/344,040, Nov. 23, 1994, abandoned.

[51] Int. Cl.$^7$ .......................................................... A61F 2/02
[52] U.S. Cl. ........................................... 424/426; 424/423
[58] Field of Search ..................................... 424/423, 426

[56] References Cited

U.S. PATENT DOCUMENTS

| | | |
|---|---|---|
| 4,164,559 | 8/1979 | Miyata et al. . |
| 4,424,208 | 1/1984 | Wallace et al. . |
| 4,582,640 | 4/1986 | Smestad et al. . |
| 4,642,117 | 2/1987 | Nguyen et al. . |
| 5,162,430 | 11/1992 | Rhee et al. . |
| 5,292,802 | 3/1994 | Rhee et al. . |
| 5,306,500 | 4/1994 | Rhee et al. . |
| 5,328,955 | 7/1994 | Rhee et al. . |
| 5,475,052 | 12/1995 | Rhee et al. . |
| 5,510,418 | 4/1996 | Rhee et al. . |
| 5,550,187 | 8/1996 | Rhee et al. . |
| 5,565,519 | 10/1996 | Rhee et al. . |

*Primary Examiner*—Carlos A. Azpuru
*Attorney, Agent, or Firm*—Morrison & Foerster, LLP

[57] ABSTRACT

The present invention discloses a novel, injectable crosslinked collagen composition which is able to continue crosslinking after injection to a soft or hard tissue site in order to anchor the collagen implant to the host tissue. The composition comprises particulate crosslinked collagen, noncrosslinked collagen (which may be fibrillar or nonfibrillar collagen), and a chemical crosslinking agent, such as synthetic hydrophilic polymer. Methods of augmenting soft or hard tissue using these injectable collagen compositions are also disclosed.

13 Claims, 3 Drawing Sheets

CROSSLINKED COLLAGEN COMPOSITIONS FOR IN SITU ADMINISTRATION

CROSS REFERENCE TO RELATED APPLICATIONS

This application is a continuation of U.S. application Ser. No. 08/730,157, filed Oct. 15, 1996, now abandoned; which is a continuation of U.S. application Ser. No. 08/344,040, filed Nov. 23, 1994, now abandoned.

FIELD OF THE INVENTION

This invention relates generally to crosslinked collagen compositions which are able to be injected and, following injection, continue to crosslink in situ, preferably anchoring the collagen implant to host tissue. Specifically, this invention relates to injectable collagen compositions comprising particulate crosslinked collagen, noncrosslinked collagen (which may be fibrillar or nonfibrillar collagen), and a chemical crosslinking agent, such as a synthetic hydrophilic polymer. Also provided are methods of tissue augmentation using such injectable collagen compositions.

BACKGROUND OF THE INVENTION

U.S. Pat. No. 4,424,208, issued Jan. 3, 1984 to Wallace et al., and commonly owned by the assignee of the present application, discloses an injectable implant material for soft tissue augmentation comprising a dispersion of particles of crosslinked atelopeptide collagen and reconstituted fibrous atelopeptide collagen in a physiologically acceptable aqueous carrier.

Commonly owned U.S. Pat. No. 4,582,640, issued Apr. 15, 1986 to Smestad et al., discloses glutaraldehyde-crosslinked collagen compositions and processes for preparing such compositions which comprise reconstituting atelopeptide collagen from solution by neutralizing the solution at a reduced temperature and a hypotonic ionic strength, crosslinking the reconstituted collagen fibers in an aqueous medium at a concentration of 0.1 to 10 mg/ml with glutaraldehyde, followed by separating the crosslinked collagen from the reaction mixture. Commonly owned U.S. Pat. No. 4,642,117, issued Feb. 10, 1987 to Nguyen et al., discloses an injectable collagen material comprised of reconstituted, mechanically sheared atelopeptide fibers obtained by passing the fibers repeatedly through a rigid mesh screen. The mechanically sheared collagen fibers may be further crosslinked, for example, with glutaraldehyde, to improve implant characteristics.

Commonly owned U.S. Pat. No. 5,162,430, issued Nov. 10, 1992 to Rhee et al., discloses collagen-synthetic polymer conjugates and methods of covalently binding collagen to synthetic hydrophilic polymers. Also disclosed in U.S. Pat. No. 5,162,430 is the general concept of conjugating to a synthetic hydrophilic polymer a collagen material that had previously been crosslinked using a chemical crosslinking agent, such as glutaraldehyde.

Commonly owned U.S. Pat. No. 5,292,802, issued Mar. 8, 1994 to Rhee et al., discloses methods for making tubes comprising collagen-synthetic polymer conjugates. Commonly owned U.S. Pat. No. 5,306,500, issued Apr. 26, 1994 to Rhee et al., discloses methods of augmenting tissue with collagen-synthetic polymer conjugates.

Commonly owned U.S. Pat. No. 5,328,955, issued Jul. 12, 1994 to Rhee et al., discloses various activated forms of polyethylene glycol and various linkages which can be used to produce collagen-synthetic polymer conjugates having a range of physical and chemical properties. Commonly owned, copending U.S. application Ser. No. 07/984,933, filed Dec. 2, 1992, discloses methods for coating implants with collagen-synthetic polymer conjugates.

Commonly owned, copending U.S. application Ser. No. 08/146,843, filed Nov. 3, 1993, discloses conjugates comprising various species of glycosaminoglycan covalently bound to synthetic hydrophilic polymers, which are optionally bound to collagen as well. Commonly owned, copending U.S. application Ser. No. 08/147,227, filed Nov. 3, 1993, discloses collagen-polymer conjugates comprising chemically modified collagens such as, for example, succinylated collagen or methylated collagen, covalently bound to synthetic hydrophilic polymers to produce optically clear materials for use in ophthalmic or other medical applications.

Commonly owned U.S. application Ser. No. 08/236,769, filed May 2, 1994, discloses collagen-synthetic polymer matrices prepared using a multiple step reaction. Commonly owned U.S. application Ser. No. 08/287,549, filed Aug. 8, 1994, discloses a method of preparing crosslinked biomaterial compositions, for use in tissue augmentation or the production of various formed implants, which method comprises mixing collagen or another biocompatible polymer with a sterile synthetic hydrophilic polymer in dry form. Also disclosed are methods of preparing dry crosslinking agents in sterile form packaged in syringes.

All publications cited above and herein are incorporated herein by reference to describe and disclose the subject matter for which it is cited.

In our earlier patents and applications, we disclosed compositions comprising synthetic hydrophilic polymers, usually various types of functionally activated polyethylene glycol (PEG), chemically conjugated to inert biomaterials, including collagen and glycosaminoglycans. A consistent problem has been encountered with such PEG-crosslinked biomaterial compositions in that the forms of activated PEG which are most useful in the formation of crosslinked collagen materials having high gel strengths tend to exhibit very short cure times (i.e., the amount of time required for a material to attain a specified value of elastic modulus or gel stiffness). For a physician providing soft tissue augmentation in the face, such as filling in wrinkles or scars, the cure time of a composition corresponds to the maximum amount of time that the material can be extruded from the needle and manipulated beneath the patient's skin following injection to minimize visible lumping and beading of the material. Short cure times result in inconveniently blocked needles and may result in unsightly (though temporary) lumps in the patient's skin due to material that has not been well distributed within the dermis.

We now disclose a detailed description of preferred embodiments of the present invention, including injectable crosslinked collagen compositions having controlled cure times and methods of using such compositions to effect augmentation of soft or hard tissue.

SUMMARY OF THE INVENTION

In accordance with the present invention, we have discovered that mixing particulate crosslinked collagen ("XC") with noncrosslinked collagen ("NX"), then crosslinking the heterogeneous collagen mixture with a chemical crosslinking agent, such as a synthetic hydrophilic polymer, results in crosslinked collagen compositions having specific properties that correlate with superior injectability, such as longer cure time and better extrudability from a syringe needle and, more specifically, from a small gauge needle such as a 30-gauge needle. These in situ crosslinkable collagen compositions generally contain between about 25 to 95 percent by weight of particulate crosslinked collagen, between about 5 to 75 percent by weight of noncrosslinked collagen, and between about 0.1 to 5 percent by weight of a chemical crosslinking agent. The term "particulate crosslinked collagen" as used herein refers to an injectable, aqueous dispersion of insoluble crosslinked collagen particles. "Improved extrudability" means that, for a given amount of cure time, less force is required to extrude the material from a syringe needle of a specified size.

These heterogeneous crosslinked collagen compositions may also show better persistence in vivo than previous crosslinked collagen compositions that were prepared using only collagen that had not been previously crosslinked as the starting material. In vivo persistence refers to the amount of time that a discrete quantity of an implanted material will last in the body prior to being dispersed and/or reabsorbed by the body.

We have also found that it is possible to manipulate specific properties of the composition by varying the relative proportions of particulate crosslinked collagen, noncrosslinked collagen, and crosslinking agent within the composition. For example, crosslinked collagen compositions containing relatively high proportions of particulate crosslinked collagen show easier extrudability, whereas compositions containing relatively high proportions of noncrosslinked collagen show greater gel strength because the smaller fibers of the noncrosslinked collagen have more sites available for crosslinking with the chemical crosslinking agent. Therefore, it is important to achieve an appropriate balance between the two forms of collagen in order to obtain a composition that has specific properties which render it superior for use as an injectable composition for tissue augmentation. Compositions intended for use in soft tissue augmentation will preferably contain between about 70 to 80 percent by weight of particulate crosslinked collagen and between about 20 to 30 percent by weight of noncrosslinked collagen; compositions for use in hard tissue augmentation (or in certain soft tissue augmentation applications, such as sphincter augmentation) will preferably contain approximately 50 to 60 percent by weight of particulate crosslinked collagen and approximately 40 to 50 percent by weight of noncrosslinked collagen.

The present invention discloses injectable collagen compositions comprising particulate crosslinked collagen, noncrosslinked collagen, and a chemical crosslinking agent. A particularly preferred composition of the invention comprises about 60 to 80 percent by weight of glutaraldehyde-crosslinked collagen, about 20 to 40 percent by weight of noncrosslinked collagen, and about 0.1 to 1.5 percent by weight of a synthetic hydrophilic polymer.

In a general method for providing tissue augmentation using compositions of the invention, a composition comprising particulate crosslinked collagen, noncrosslinked collagen, and a chemical crosslinking agent is injected to a tissue site in need of augmentation before substantial crosslinking has occurred between the collagen and the crosslinking agent. A preferred method for providing tissue augmentation comprises providing a syringe containing a mixture of glutaraldehyde-crosslinked collagen and non-crosslinked collagen, providing a syringe containing a synthetic hydrophilic polymer, mixing the contents of the two syringes, and injecting the resulting composition to a tissue site in need of augmentation before substantial crosslinking has occurred between the collagen and the synthetic hydrophilic polymer.

The compositions of the present invention have many improved features over previous injectable biomaterial compositions, such as superior injectability, longer extrudability and, possibly, greater persistence, which make the compositions especially well-suited for use in tissue augmentation. Additional features and advantages of the invention will become apparent upon reading the detailed description of the invention which follows.

DEFINITIONS

Figure 1:
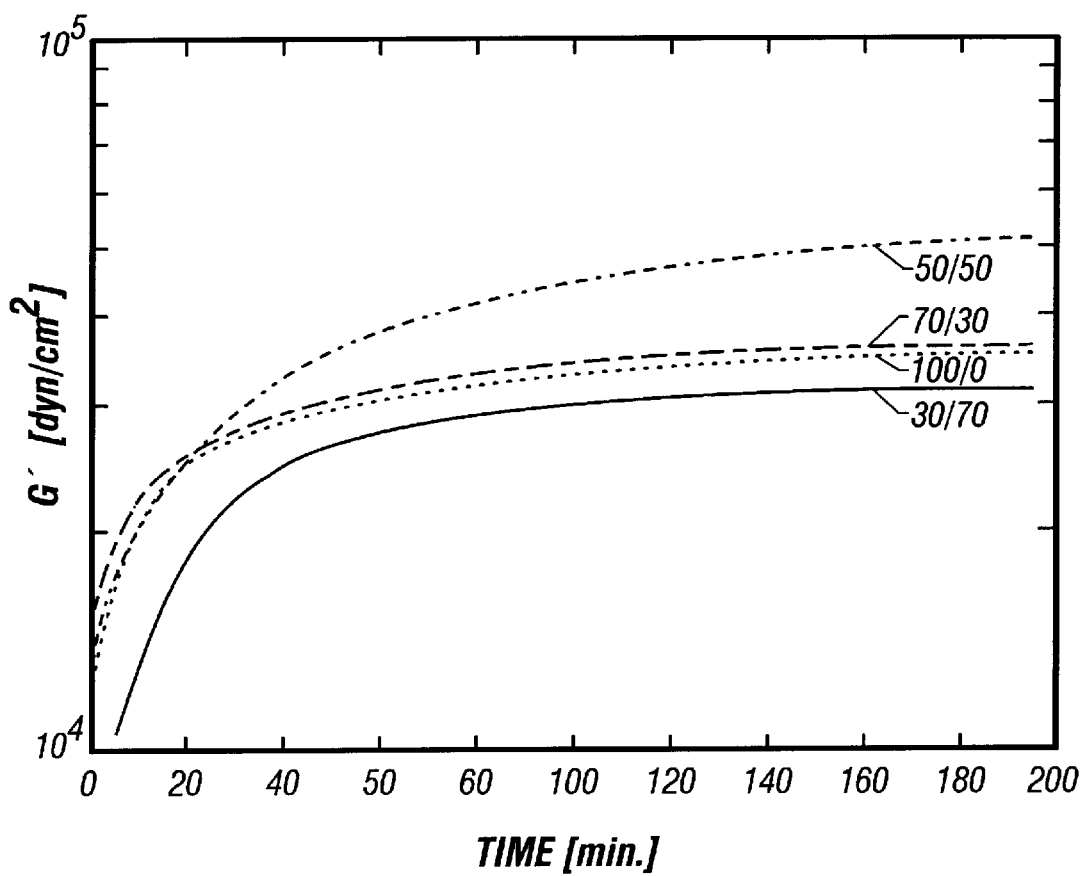
FIG. 1 shows cure profiles for collagen compositions containing glutaraldehyde-crosslinked collagen (35 mg/ml collagen concentration) and noncrosslinked collagen (35 mg/ml collagen concentration), in ratios of 100:0, 70:30, 50:50, and 30:70 by weight, and 0.1% by weight of difunctionally activated SG-PEG (3800 MW).

It must be noted that, as used in this specification and the appended claims, the singular forms "a","an", and "the" include plural referents unless the context clearly dictates otherwise. For example, reference to "a conjugate" includes one or more conjugate molecules, reference to "an article" includes one or more different types of articles known to those skilled in the art and reference to "the collagen" includes mixtures of different types of collagens and so forth.

Specific terminology of particular importance to the description of the present invention is defined below:

The term "aqueous carrier" refers to a water-based fluid carrier, such as water-for-injection (WFI) or a solution of phosphate-buffered saline (PBS).

The term "atelopeptide collagen" refers to collagens which have been chemically treated or otherwise processed to remove the telopeptide regions, which are known to be responsible for causing an immune response in humans to collagens from other animal, such as bovine, sources.

The terms "chemically conjugated" and "conjugated" as used herein mean attached through a covalent chemical bond. In the practice of the invention, a hydrophilic synthetic polymer and a biocompatible polymer molecule may be covalently conjugated directly to each other by means of a functional group on the synthetic hydrophilic polymer, or the biocompatible polymer and the synthetic polymer may be covalently conjugated using a linking radical, so that the hydrophilic synthetic polymer and the biocompatible polymer are each bound to the radical, but not directly to each other.

The term "chemical crosslinking agent" as used herein refers to any chemical agent capable of covalently binding collagen to form a crosslinked collagen network.

The term "collagen" as used herein refers to all types and forms of collagen, including those which have been recombinantly produced, extracted from naturally occurring sources (such as bovine corium or human placenta), processed, or otherwise modified.

The term "collagen suspension" refers to a suspension of noncrosslinked or crosslinked collagen fibers in an aqueous carrier, such as water or phosphate-buffered saline (PBS) solution.

The term "collagen-synthetic polymer" refers to collagen chemically conjugated to a synthetic hydrophilic polymer, within the meaning of this invention. For example, "PEG-collagen" denotes a composition of the invention wherein molecules of collagen are covalently conjugated to molecules of polyethylene glycol (PEG).

The term "difunctionally activated" refers to synthetic hydrophilic polymer molecules which have been chemically derivatized so as to have two functional groups capable of reacting with primary amino groups on biocompatible polymer molecules, such as collagen or deacetylated glycosaminoglycans. The two functional groups on a difunctionally activated synthetic hydrophilic polymer are generally located at opposite ends of the polymer chain. Each functionally activated group on a difunctionally activated synthetic hydrophilic polymer molecule is capable of covalently binding with a biocompatible polymer molecule, thereby effecting crosslinking between the biocompatible polymer molecules.

The term "dry" means that substantially all unbound water has been removed from a material.

The term "fibrillar collagen" refers to collagens in which the triple helical molecules aggregate to form thick fibers due to intermolecular charge and hydrophobic interactions.

The term "functionally activated" refers to synthetic hydrophilic polymers which have been chemically derivatized so as to have one or more functional group capable of reacting with primary amino groups on biocompatible polymer molecules.

The term "in situ" as used herein means at the site of administration.

The term "in situ crosslinking" as used herein refers to crosslinking of a biocompatible polymer implant following implantation to a tissue site on a human or animal subject, wherein at least one functional group on the synthetic polymer is covalently conjugated to a biocompatible polymer molecule in the implant, and at least one functional group on the synthetic polymer is free to covalently bind with other biocompatible polymer molecules within the implant, or with collagen molecules within the patient's own tissue.

The term "molecular weight" as used herein refers to the weight average molecular weight of a number of molecules in any given sample, as commonly used in the art. Thus, a sample of PEG 2000 might contain a statistical mixture of polymer molecules ranging in weight from, for example, 1500 to 2500, with one molecule differing slightly from the next over a range. Specification of a range of molecular weight indicates that the average molecular weight may be any value between the limits specified, and may include molecules outside those limits. Thus, a molecular weight range of about 800 to about 20,000 indicates an average molecular weight of at least about 800, ranging up to about 20,000.

The term "multifunctionally activated" refers to synthetic hydrophilic polymers which have been chemically derivatized so as to have two or more functional groups which are located at various sites along the polymer chain and are capable of reacting with primary amino groups on biocompatible polymer molecules. Each functional group on a multifunctionally activated synthetic hydrophilic polymer molecule is capable of covalently binding with a biocompatible polymer molecule, thereby effecting crosslinking between the biocompatible polymer molecules. Types of multifunctionally activated hydrophilic synthetic polymers include difunctionally activated, tetrafunctionally activated, and star-branched polymers.

The term "noncrosslinked collagen" refers to collagens that have not been previously crosslinked using chemical crosslinking agents. Such noncrosslinked collagens may include both fibrillar and nonfibrillar collagens.

The term "nonfibrillar collagen" refers to collagens in which the triple helical molecules do not aggregate to form thick fibers, such that a composition containing nonfibrillar collagen will be optically clear.

The terms "synthetic hydrophilic polymer" or "synthetic polymer" refer to polymers which have been synthetically produced and which are hydrophilic, but not necessarily water-soluble. Examples of synthetic hydrophilic polymers which can be used in the practice of the present invention are polyethylene glycol (PEG), polyoxyethylene, polymethylene glycol, poly-trimethylene glycols, polyvinylpyrrolidones, polyoxyethylene-polyoxypropylene block polymers and copolymers, and derivatives thereof. Naturally occurring polymers such as proteins, starch, cellulose, heparin, hyaluronic acid, and derivatives thereof are expressly excluded from the scope of this definition.

The term "tissue augmentation" as used herein refers to the replacement or repair of defects in the soft or hard tissues of a human body.

Except as otherwise defined above, all technical and scientific terms used herein have the same meaning as commonly understood by one of ordinary skill in the art to which this invention belongs. Although any methods and materials similar or equivalent to those described herein may be useful in the practice or testing of the present invention, only the preferred methods and materials are described below. It is not intended that the invention be limited to these preferred embodiments, however. The invention is intended to have the scope defined by the attached claims.

DETAILED DESCRIPTION OF THE PREFERRED EMBODIMENTS OF THE INVENTION

In accordance with the present invention, in situ crosslinkable, injectable collagen compositions are described which offer improved handling and use characteristics, particularly for soft tissue end use applications. In order to prepare the in situ crosslinkable collagen compositions of the present invention, it is first necessary to provide both particulate crosslinked collagen and noncrosslinked collagen.

In general, collagen from any source may be used as the starting material to prepare the compositions of the invention; for example, collagen may be extracted and purified from human or other mammalian source, or may be recombinantly or otherwise produced. Collagen of any type, including, but not limited to, types I, II, III, IV, or any combination thereof, may be used, although type I is generally preferred. Either atelopeptide or telopeptide-containing collagen may be used; however, when collagen from a xenogeneic source, such as bovine collagen, is used, atelopeptide collagen is generally preferred, because of its reduced immunogenicity compared to telopeptide-containing collagen. The collagen should be in a pharmaceutically pure form such that it can be incorporated into a human body without generating any significant immune response.

Particulate crosslinked collagens for use in the present invention include collagens that have been previously crosslinked using any acceptable method for crosslinking collagen known in the art, including, without limitation, heat, irradiation, and chemical crosslinking agents such as aldehydes, divinyl sulfone, epoxides, carbodiimides, imidazole, synthetic hydrophilic polymers such as functionally activated polymeric glycols, or mixtures of these crosslinking agents. Collagen crosslinked using synthetic hydrophilic polymers, such as PEG-crosslinked collagen, can be prepared according to the methods disclosed in U.S. Pat. No. 5,162,430.

Aldehydes which may be used to prepare particulate crosslinked collagen for use in the present invention include, without limitation, glutaraldehyde, formaldehyde, acetaldehyde, glyoxal pyruvic aldehyde, and dialdehyde starch, with glutaraldehyde being particularly preferred. Glutaraldehyde-crosslinked collagen may be prepared using fibrillar collagen according the methods described, for example, in U.S. Pat. Nos. 4,582,640 and 4,642,117. When preparing glutaraldehyde-crosslinked collagen, care must be taken to remove residual, unbound glutaraldehyde from the crosslinked collagen, because glutaraldehyde itself is toxic to the human body.

In general, when glutaraldehyde-crosslinked collagen is prepared according to the methods of the above-referenced patents, only about 10 percent or less of the lysine residues on the collagen will be bound by glutaraldehyde molecules, leaving a substantial number of lysine residues available for subsequent crosslinking with molecules of a synthetic hydrophilic polymer. Glutaraldehyde-crosslinked collagen for use in the present invention is normally present in an aqueous suspension having a collagen concentration within the range of about 10 mg/ml to about 90 mg/ml, preferably, between about 20 mg/ml to about 70 mg/ml. Glutaraldehyde-crosslinked collagen in suspension at a collagen concentration of 35 mg/ml is commercially available from Collagen Corporation (Palo Alto, Calif.) under the trademark Zyplast® Collagen.

Noncrosslinked collagens for use in the present invention may be in the fibrillar or nonfibrillar form, but fibrillar collagens are generally preferred for tissue augmentation applications due to their increased persistence in vivo. However, nonfibrillar collagens, including chemically modified collagens such as succinylated or methylated collagen, may be preferable in certain situations, such as ophthalmic applications where an optically transparent material is required. Succinylated and methylated collagens can be prepared according to the methods described in U.S. Pat. No. 4,164,559. Noncrosslinked collagens for use in the present invention are normally in aqueous suspension at a concentration between about 20 mg/ml to about 120 mg/ml, preferably, between about 30 mg/ml to about 80 mg/ml. Fibrillar collagen in suspension at various collagen concentrations is also commercially available from Collagen Corporation under the trademark Zyderm® I Collagen (35 mg/ml) and Zyderm II Collagen (65 mg/ml).

Synthetic hydrophilic polymers, such as functionally activated polyethylene glycols, are the preferred chemical crosslinking agents for use in the in situ crosslinkable collagen compositions of the invention. However, other chemical crosslinking agents including, without limitation, aldehydes, divinyl sulfone, epoxides, carbodiimides, imidazole, and mixtures thereof, may be used in the practice of the invention. As many of these crosslinking agents have toxic effects on the human body, only very small quantities of such agents should be employed in collagen compositions intended for in situ crosslinking. Crosslinking agents which tend to be more toxic are more suitable for use in preparing crosslinked collagen compositions for use in formed implants, in which case residual, unbound crosslinking agent can be removed from the composition prior to incorporation of the implant into the body of a patient.

Due to their biocompatibility and low immunogenicity, functionally activated polyethylene glycols are the preferred chemical crosslinking agents for use in preparing the in situ crosslinkable compositions of the present invention. Various activated forms of polyethylene glycol are described below.

Specific Forms of Activated Polyethylene Glycol

For use in the present invention, molecules of polyethylene glycol are chemically modified in order to provide functional groups on one or, preferably, two or more sites along the length of the PEG molecule, so that covalent binding can occur between the PEG and reactive groups on the collagen. Some specific activated forms of PEG are shown structurally below, as are generalized reaction products obtained by reacting activated forms of PEG with collagen. In Formulas 1–7, the term COL represents collagen (which may be particulate crosslinked or non-crosslinked collagen). The term PEG represents polymers having the repeating structure $(OCH_2\ CH_2)_n$.

The first activated PEG is difunctionally activated PEG succinimidyl glutarate, referred to herein as (SG-PEG). The structural formula of this molecule and the reaction product obtained by reacting it with collagen are shown in Formula 1.

SG-PEG: Difinctionally Activated PEG Succinimidyl Glutarate

FORMULA 1

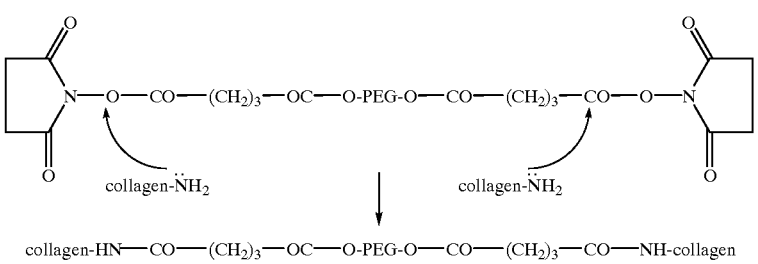

Another difunctionally activated form of PEG is referred to as PEG succinimidyl (S-PEG). The structural formula for this compound and the reaction product obtained by reacting it with collagen is shown in Formula 2. In a general structural formula for the compound, the subscript 3 is replaced with an "n". In the embodiment shown in Formula 1, n=3, in that there are three repeating $CH_2$ groups on either side of the PEG.

The structure in Formula 2 results in a conjugate which includes an "ether" linkage which is less subject to hydrolysis. This is distinct from the conjugate shown in Formula 1, wherein an ester linkage is provided. The ester linkage is subject to hydrolysis under physiological conditions.

S-PEG, n=3: Difunctionally Activated PEG Succinimidyl

FORMULA 2

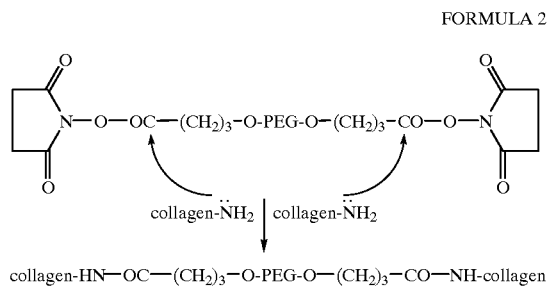

Yet another difunctionally activated form of polyethylene glycol, wherein n=2, is shown in Formula 3, as is the conjugate formed by reacting the activated PEG with collagen.

S-PEG, n=2: Difunctionally Activated PEG Succinimidyl

FORMULA 3

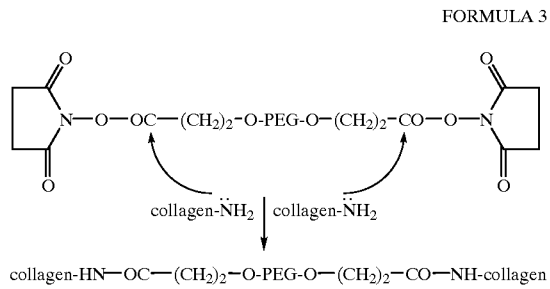

Another preferred embodiment of the invention similar to the compounds of Formulas 2 and 3 is provided when n=1. The structural formula and resulting collagen-synthetic polymer conjugate are shown in Formula 4. It is noted that this conjugate includes both an ether and a peptide linkage. These linkages are stable under physiological conditions.

S-PEG, n=1: Difunctionally Activated PEG Succinimidyl

FORMULA 4

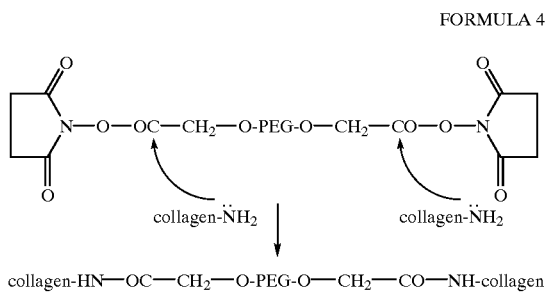

Another difunctionally activated form of PEG is referred to as PEG succinimidyl succinamide (SSA-PEG). The structural formula for this compound and the reaction product obtained by reacting it with collagen is shown in Formula 5. In the structure shown in Formula 1, n=2; however, related compounds, wherein n=1 or n=3–10, may also be used in the practice of the invention.

The structure in Formula 5 results in a conjugate which includes an "amide" linkage which, like the ether linkage previously described, is less subject to hydrolysis and is therefore more stable than an ester linkage.

SSA-PEG, n=2: Difunctionally Activated PEG Succinimidyl Succinamide

FORMULA 5

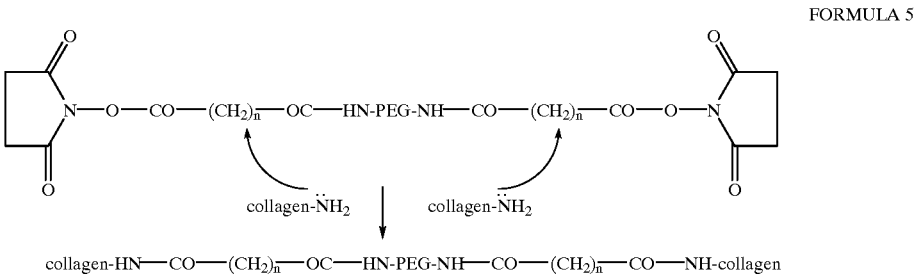

Yet another difunctionally activated form of PEG is provided when n=0. This compound is referred to as PEG succinimidyl carbonate (SC-PEG). The structural formula of this compound and the conjugate formed by reacting SC-PEG with collagen is shown in Formula 6.

SC-PEG, n=0: Difunctionally Activated PEG Succinimidyl Carbonate

FORMULA 6

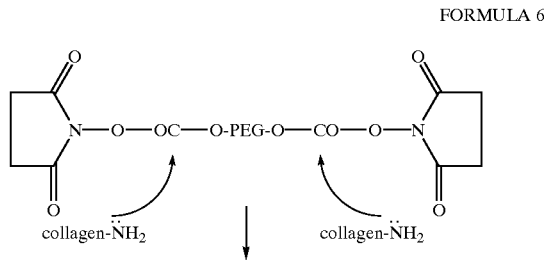

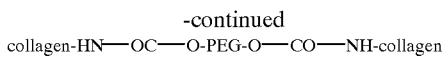

All of the activated polyethylene glycol derivatives depicted in Formulas 1–6 involve the inclusion of the succinimidyl group. However, different activating groups can be attached at sites along the length of the PEG molecule. For example, PEG can be derivatized to form difunctionally activated PEG propion aldehyde (A-PEG), which is shown in Formula 7, as is the conjugate formed by the reaction of A-PEG with collagen. The linkage shown in Formula 6 is referred to as a —$(CH_2)_n$—NH— linkage, where n=1–10.

A-PEG: Difunctionally Activated PEG Propion Aldehyde

FORMULA 7

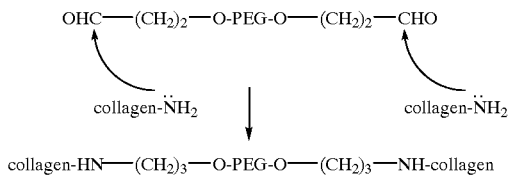

Yet another form of activated polyethylene glycol is difunctionally activated PEG glycidyl ether (E-PEG), which is shown in Formula 8, as is the conjugate formed by reacting such with collagen.

E-PEG: Difunctionally Activated PEG Glycidyl Ether

FORMULA 8

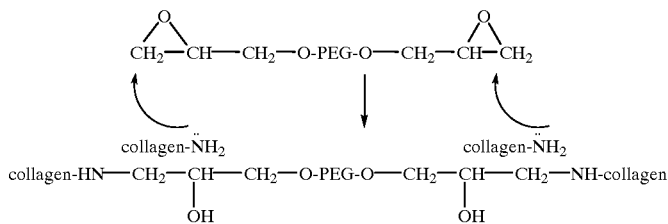

Many of the activated forms of polyethylene glycol described above are now available commercially from Shearwater Polymers, Huntsville, Ala., and Union Carbide, South Charleston, W.Va. The various activated forms of polyethylene glycol and various linkages which can be used to produce collagen-synthetic polymer conjugates having a range of physical and chemical properties are described in further detail in commonly owned U.S. Pat. No. 5,328,955.

The concentration of chemical crosslinking agent used in the practice of the invention will vary depending upon a number of factors, including the type and molecular weight of the crosslinking agent used, the relative proportions and collagen concentrations of the particulate crosslinked collagen and noncrosslinked collagen used, and the degree of crosslinking and ease of injectability desired. In general, we have found that chemical crosslinking agent concentrations in the range of about 0.1 to about 5 percent by weight of the final composition are preferred for use in the present invention. The preferred crosslinking agent concentration when functionally activated polyethylene glycols (PEGs) are used is in the range of about 0.1 to about 1.5 percent (based on dry polymer weight) by weight of the final composition. For example, a final composition having a total weight of 1 gram (1000 milligrams) would contain between about 1 to about 15 milligrams of functionally activated PEG.

Mixtures of different types of chemical crosslinking agents (for example, a functionally activated polyethylene glycol and another type of crosslinking agent) may also be employed in the preparation of compositions of the present invention. Mixing different types of crosslinking agents will result in crosslinked collagen compositions having varying properties.

Preparation of in situ Crosslinkable Collagen Compositions

In a preferred method for preparing the compositions of the invention, particulate crosslinked collagen and non-crosslinked collagen are mixed together in appropriate proportions and dispensed into syringes. The particulate crosslinked collagen ("XC") should comprise between about 25 to about 95 percent, preferably, between about 60 to about 80 percent by weight of the final composition. Non-crosslinked collagen ("NX") should comprise between about 5 to about 75, preferably, between about 20 to about 40 percent by weight of the final composition.

Synthetic hydrophilic polymers are the preferred chemical crosslinking agents for use in the compositions and methods of the invention. Synthetic hydrophilic polymers for use in the present invention are preferably multifunctionally activated and, more preferably, difunctionally activated. Preferred polymers are difunctionally activated forms of SG-PEG (as shown in Formula 1, above), S-PEG (n=1–3, shown in Formulas 2–4), SSA-PEG (n=1–10, shown in Formula 5), and SC-PEG (n=0, shown in Formula 6). As described previously, reaction of SG-PEG with collagen results in collagen-synthetic polymer conjugates containing the ester linkage; reaction of S-PEG (n=1–3) or SC-PEG (n=0) with collagen results in conjugates containing the ether linkage; and reaction of SSA-PEG (n=1–10) with collagen results in conjugates containing the amide linkage.

Synthetic hydrophilic polymers for use in the present invention are generally provided in sterile, dry form, packaged in syringes. The synthetic polymer may be mixed in dry form with the collagen. Alternatively, the dry polymer can be dissolved in an aqueous carrier immediately prior to mixing with the collagen, but this is generally not a preferred method, due to loss of polymer activity as a result of hydrolysis.

The collagen and crosslinking agent (in dry form or aqueous solution) are generally mixed by connecting the syringe containing the collagen with the syringe containing the synthetic polymer using a syringe connector (such as three-way stopcock) and passing the material back and forth between the two syringes until the material is adequately mixed (usually requiring a minimum of about 20 passes, with one pass being counted each time the volume of material passes through the syringe connector).During the mixing process, crosslinking is initiated between molecules of the collagen and the crosslinking agent, leading to the formation of several different types of covalently bound collagen conjugates. For example, when a difunctionally activated polyethylene glycol is used, possible conjugate combinations include: NX - PEG - NX, XC - PEG - XC, and NX - PEG - XC. There may also be conjugates in which only one of the two functional ends (represented by "*") of the PEG molecule is linked with a collagen molecule; for example, NX - PEG - * and XC - PEG - *. These types of conjugates have one remaining functional group capable of binding to lysine residues on collagen molecules within a patient's own tissue, serving to anchor the collagen implant to the tissue.

When the collagen and the crosslinking agent have been adequately mixed, all of the material is transferred into one of the two syringes or, alternatively, into a third syringe. The material may be extruded from the syringe until the point in time at which an equilibrium crosslinked network has been formed between the collagen and the crosslinking agent (usually, on the order of about 30 to about 60 minutes when a functionally activated PEG is used). The time required for formation of an equilibrium crosslinked network is generally referred to as the "cure time" of a material and is measured as the amount of time required for the material to attain a specified value of elastic modulus. A number of factors can affect the cure time of a particular material, including the type and concentration of the crosslinking agent used, the collagen concentrations of the particulate crosslinked collagen and noncrosslinked collagen used, and the temperature and pH of the materials.

Figure 2:
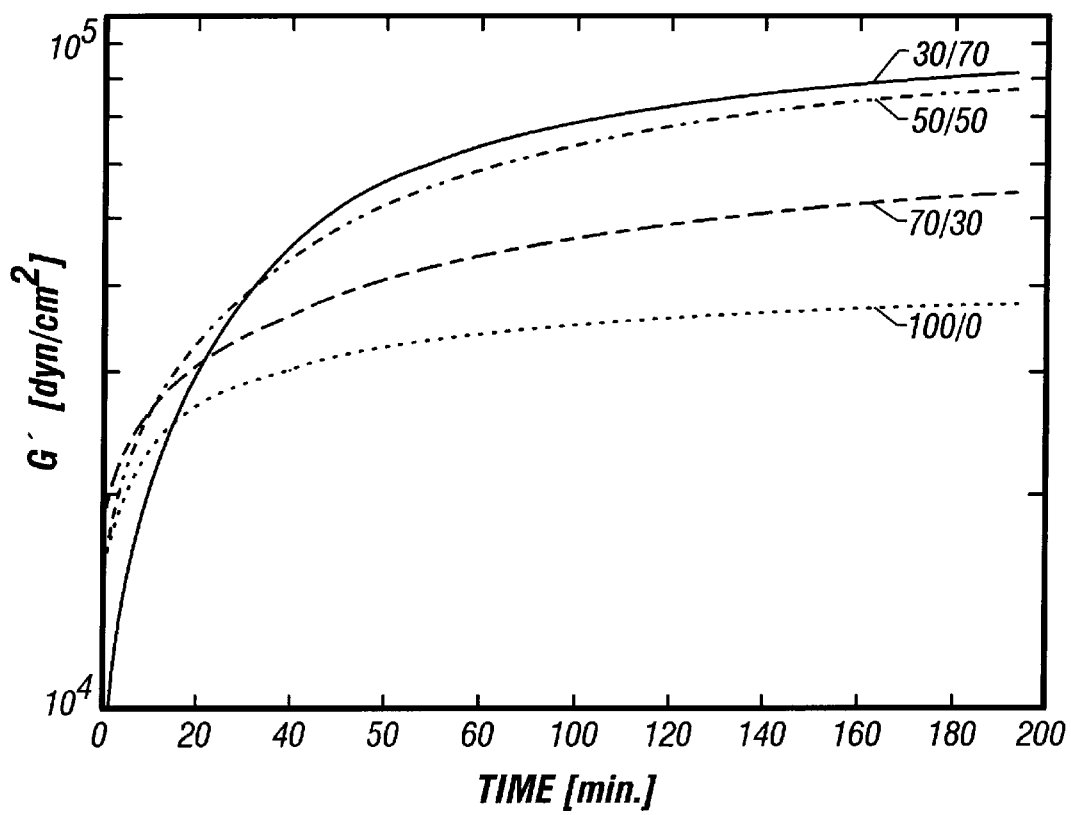
FIG. 2 shows cure profiles for collagen compositions containing glutaraldehyde-crosslinked collagen (35 mg/ml collagen concentration) and noncrosslinked collagen (35 mg/ml collagen concentration), in ratios of 100:0, 70:30, 50:50, and 30:70 by weight, and 0.3% by weight of difunctionally activated SG-PEG (3800 MW).
Figure 3:
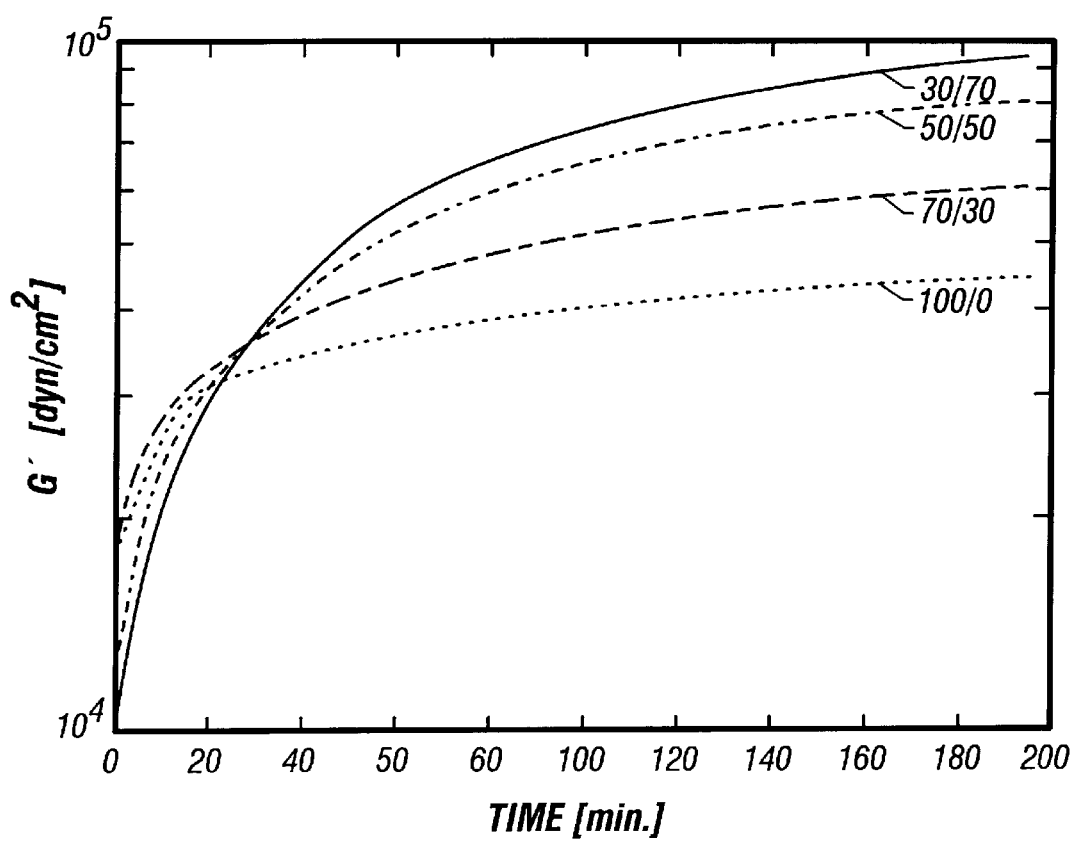
FIG. 3 shows cure profiles for collagen compositions containing glutaraldehyde-crosslinked collagen (35 mg/ml collagen concentration) and noncrosslinked collagen (35 mg/ml collagen concentration) in ratios of 100:0, 70:30, 50:50, and 30:70 by weight, and 0.5% by weight of difunctionally activated SG-PEG (3800 MW).

For the purpose of the present invention, an important factor in determining cure time is the relative proportion of particulate crosslinked collagen to noncrosslinked collagen in the composition. For example, compositions containing higher proportions (for example, 40 to 50 percent by weight) of noncrosslinked collagen will achieve equivalent elastic moduli (i.e., gel stiffness) in shorter times than compositions having lower proportions (e.g., 20 to 30 percent by weight) of noncrosslinked collagen. FIGS. 1–3 show cure profiles for crosslinked collagen compositions as a function of the relative concentrations of particulate crosslinked collagen to noncrosslinked collagen; this information is discussed in detail in Example 3.

If the material is injected to a tissue site before equilibrium crosslinking (curing) has occurred, functional groups on the crosslinking agent may bind to collagen molecules in the host tissue (as described above), thereby providing biological anchoring of the collagen implant to the host tissue. Collagen implants which have been "biologically anchored" to host collagen are more difficult to displace and therefore may show greater persistence in vivo than currently available injectable collagen implants. Thus, although the practitioner using the composition has a longer time period after mixing the components of the composition in which the composition may be injected, he/she may wish to inject the composition into a tissue site shortly after mixing in order to achieve better biological anchoring of the implant material to the patient's own tissue.

USE AND ADMINISTRATION

In a preferred method for providing soft tissue augmentation, a physician is provided with a kit containing the following: one 1-cc syringe containing a mixture of glutaraldehyde-crosslinked collagen (GAX) and non-crosslinked collagen in appropriate proportions (for example, 70% GAX and 30% noncrosslinked collagen); one 3-cc syringe containing a sterile, dry, synthetic hydrophilic polymer, which is preferably a functionally activated polyethylene glycol; one syringe connector; and one or more 27-gauge or smaller (preferably 30-gauge) needles.

The physician connects the syringe containing the collagen mixture with the syringe containing the dry synthetic polymer by means of the syringe connector. He/she then mixes the collagen and synthetic polymer back and forth between the syringes by employing at least 20, and, preferably, at least 30, passes of material between the syringes. When the collagen and synthetic polymer have been adequately mixed, the physician transfers all of the material into the 1-cc syringe (which formerly contained the collagen mixture), detaches the empty syringe from the syringe connector, attaches one of the needles to the syringe containing the material, then proceeds to inject the material to a tissue site in need of augmentation using the serial injection technique. After each injection, the physician gently massages the site of injection to distribute the material evenly beneath the skin to prevent unsightly lumping and beading. Depending upon the specific formulation used, the injection and manipulation process may be performed for a period of 30 to 60 minutes after mixing the collagen and synthetic polymer before equilibrium crosslinking (curing) of the material has occurred. After equilibrium crosslinking has occurred, the material will be extremely difficult, if not impossible, to extrude from the syringe needle and will not be easy to manipulate within the dermis.

In addition to providing soft tissue augmentation in the face, the compositions of the present invention can also be used for soft tissue augmentation in other areas of the body, such as the urinary, anal, and esophageal sphincters, or for injectable hard tissue augmentation, such as in the non-surgical correction of a bony defect. Because these applications do not require the delicate technique of facial soft tissue augmentation and generally do not take as much time, the specific collagen composition used may contain a higher proportion of noncrosslinked collagen (for example, 40 to 50 percent by weight) than those used in the correction of facial defects. Crosslinked collagen compositions containing higher relative proportions of noncrosslinked collagen also tend to have greater gel strengths than those containing high proportions of particulate crosslinked collagen. For hard tissue applications or soft tissue applications such as sphincter augmentation, a larger needle, such as an 18-, 22-, or 25-gauge needle, may be employed.

The compositions of the present invention can also be used in the production of formed implants for a variety of medical applications, such as tubular implants for use as vascular grafts or stents. After the collagen and crosslinking agent have been adequately mixed, the material is extruded from the syringe orifice (no needle) into molds of the desired size and shape. The material should be removed from the mold only after adequate time has elapsed to allow for equilibrium crosslinking to occur between the collagen and crosslinking agent. If necessary, residual, unbound crosslinking agent can be removed from the implant prior to its incorporation into the body of a patient.

Alternatively, the collagen/crosslinking agent mixture can be extruded onto one or more surface of a preformed synthetic implant, such as a bone prosthesis or synthetic vascular graft or stent, and allowed to crosslink in place, thereby providing a crosslinked, nonimmunogenic collagen coating on the surface of the implant. Formed implants and implant coatings prepared using the compositions of the present invention may show improved persistence in vivo due to the presence of the GAX in the formulation.

EXAMPLES

The following examples are put forth so as to provide those of ordinary skill in the art with a complete disclosure and description of how to make the preferred embodiments of the conjugates, compositions, and devices and are not intended to limit the scope of what the inventors regard as their invention. Efforts have been made to ensure accuracy with respect to numbers used (e.g., amounts, temperature, molecular weight, etc.) but some experimental errors and deviation should be accounted for. Unless indicated otherwise, parts are parts by weight, molecular weight is weight average molecular weight, temperature is in degrees Centigrade, and pressure is at or near atmospheric.

Example 1 (Gel Strength of Crosslinked Collagen Compositions)

Mixtures of Zyplast® Collagen (35 mg/ml collagen concentration) (hereinafter referred to as GAX) and Zyderm® I Collagen (35 mg/ml collagen concentration (hereinafter referred to as NX) were prepared having the following weight ratios of GAX to NX: 0:100, 25:75, 50:50, and 75:25. One (1) milliliter of each of the four collagen mixtures was dispensed into a 1-cc syringe. Three (3) milligrams of dry, sterile, difunctionally activated SG-PEG (DSG-PEG, 3800 MW) was dispensed into each of four 3-cc syringes. The contents of each of the four collagen-containing 1-cc syringes was mixed with that of a corresponding PEG-containing 3-cc syringe, using at least 30 passes in each case. The material was transferred back into the 1-cc syringe (which formerly held the collagen mixture) and allowed to crosslink for approximately 16 hours at 37° C.

The tip ends of the four syringes were cut off and the respective gels extruded from the resulting orifices. The 8.5-mm diameter gel cylinders were sliced into 5-mm thick disks, which were compressed to failure in the Instron Universal Tester, Model 4202, at a constant rate of 2 millimeters per minute. Rupture forces (in Newtons) for individual disks, as well as average rupture forces and standard deviations for each of the four gels, are presented in Table 1, below.

TABLE 1

Gel Strength (in Newtons) of Crosslinked Collagen Compositions
Ratio of GAX to NX

|  | 0:100 | 25:75 | 50:50 | 75:25 |
|---|---|---|---|---|
|  | 26.3 | 39.8 | 23.3 | 11.8 |
|  | 37.9 | 31.0 | 23.2 | 12.2 |
|  | 33.4 | 26.6 | 23.1 | 7.9 |
|  | 42.0 | 41.2 | 31.3 | 9.0 |
|  | 46.1 | 41.4 | 30.0 | 13.1 |
|  | 34.1 | 30.0 | — | — |
|  | 42.6 | — | — | — |
|  | 35.1 | — | — | — |
| n = | 8 | 6 | 5 | 5 |
| Average = | 37.2 | 35.0 | 26.2 | 10.6 |
| SD = | 6.3 | 6.5 | 4.1 | 2.0 |

As shown above, the crosslinked collagen gels containing 100% and 75% noncrosslinked collagen demonstrated substantially equivalent gel strengths. In general, gel strength decreases with increasing GAX concentration. This is an unexpected result, as one skilled in the art might expect that increasing the relative amount of pre-crosslinked collagen prior to crosslinking with the DSG-PEG might reinforce the gel, resulting in crosslinked collagen compositions with greater gel strengths. However, it is now believed that a high concentration of particulate crosslinked collagen (GAX) in the collagen mixture prevents the formation of large crosslinked networks of material by confining the regions of space over which the crosslinked networks can be built, resulting in gels which show better extrudability, but weaker gel strength than gels having lower concentrations of particulate crosslinked collagen.

Example 2 (Extrusion Force of Crosslinked Collagen Compositions)

Mixtures of Zyplast® and Zyderm® I Collagens were prepared having the following weight ratios of GAX to AX: 50:50, 60:40, 70:30, and 80:20. One (1) milliliter each of the four collagen mixtures was dispensed into twelve 1-cc syringes. The contents of each syringe was then mixed using syringe-to-syringe mixing with the contents of a 3-cc syringe containing either 1, 3, or 5 milligrams (i.e., 0.1, 0.3, or 0.5% by weight, respectively) of dry, sterile, DSG-PEG (3800 MW). The material was transferred back into the 1-cc syringe (which formerly held the collagen mixture). Two samples were prepared of each material.

After 30 minutes incubation at room temperature, either a 27- or a 30-gauge needle was attached to each syringe. The force required to extrude the material from the syringe at a constant rate of 50 millimeters per minute was measured using the Instron Universal Tester, Model 4202. Mean extrusion forces (in Newtons) and mean peak-to-peak spike amplitudes are reported in Table 2, below.

TABLE 2

Extrusion Force (in Newtons) for Crosslinked Collagen Compositions

| GAX/NX Ratio | % DSG-PEG | Needle Gauge | Mean Extrusion Force (N)* | Peak-to-Peak Spike Amplitude |
|---|---|---|---|---|
| 50:50 | 0.1 | 27 | 14 | 1 |
|  |  | 30 | 22 | 1 |
|  | 0.3 | 27 | 37.5 | 5 |
|  |  | 30 | 47.5 | 5 |
|  | 0.5 | 27 | 41 | 5 |
|  |  | 30 | 50 | 5** |
| 60:40 | 0.1 | 27 | 13 | 1 |
|  |  | 30 | 19 | 1 |
|  | 0.3 | 27 | 21 | 2 |
|  |  | 30 | 29.5 | 4 |
|  | 0.5 | 27 | 24 | 3 |
|  |  | 30 | 33 | 4 |
| 70:30 | 0.1 | 27 | 10 | 1 |
|  |  | 30 | 15 | 1 |
|  | 0.3 | 27 | 16.5 | 2 |
|  |  | 30 | 22 | 2 |
|  | 0.5 | 27 | 20.5 | 3 |
|  |  | 30 | 26.5 | 4 |
| 80:20 | 0.1 | 27 | 9 | 1 |
|  |  | 30 | 13.5 | 1 |
|  | 0.3 | 27 | 14 | 2 |
|  |  | 30 | 20.5 | 3 |
|  | 0.5 | 27 | 14.5 | 2 |
|  |  | 30 | 22 | 3 |

*n = 2.
**Syringe blockage occurred and the material was no longer extrudable through the syringe needle.

Acceptable extrusion forces are generally in the range of 40 Newtons or less and, preferably, 25 Newtons or less. Therefore, as shown in the table above, all of the formulations tested showed extrusion forces within the range of acceptability, with the exception of the 50:50 formulations containing 0.3 and 0.5% DSG-PEG. In general, the force required to extrude the material through the needle decreased with increasing GAX content and decreasing DSG-PEG content. As expected, forces required to extrude materials through 30-gauge needles were higher than those required for extrusion of materials through 27-gauge needles.

Example 3 (Cure Times of Crosslinked Collagen Compositions)

Mixtures of Zyplast® and Zyderm® I Collagens were prepared having the following weight ratios of GAX to NX: 100:0, 70:30, 50:50, and 30:70. The collagen formulations were then crosslinked using dry, sterile, DSG-PEG (3800 MW) at concentrations of 0.1, 0.3, or 0.5% by weight. Elastic modulus (G') was tracked for each of the formulations over a 1 period of 200 minutes (3 hours, 20 minutes) after mixing. Cure profiles for collagen compositions containing 0.1, 0.3, and 0.5% DSG-PEG are presented in FIGS. 1, 2, and 3, respectively.

As shown in Table 2, it has been experimentally determined that crosslinked collagen formulations having an elastic modulus (gel stiffness) of about $4 \times 10^4$ dynes/cm$^2$ or less are extrudable through 30-gauge needles. Materials having an elastic modulus greater than about $4 \times 10^4$ dynes/cm$^2$ generally result in blocked needles when a 30-gauge needle is used. Therefore, for the purposes of this experiment, cure time is defined as the amount of time required for the material to achieve a specified value of elastic modulus of $4 \times 10^4$ dynes/cm$^2$, that is, the amount of time that the material is still extrudable through a 30-gauge needle. Naturally, if a larger gauge needle is used, a material having a higher elastic modulus could be tolerated.

In general, cure times (time required for the material to reach an elastic modulus of $4 \times 10^4$ dynes/cm$^2$) increased with increasing GAX concentration, i.e., collagen formulations containing 100% GAX had the longest cure times and those containing only 30% GAX had the shortest cure times. The one exception to this general rule is seen in FIG. 1, where the collagen formulation containing 30% GAX had the longest cure time of the four formulations. This is due to the fact that the DSG-PEG concentration was too low to achieve formation of a robust network structure with the noncrosslinked collagen.

As demonstrated by the cure profiles shown in FIGS. 1–3, in general (with the one exception described above), formulations containing 70% and 100% GAX were still injectable after 30 minutes (that is, they had elastic moduli of $4 \times 10^4$ dynes/cm$^2$ or less 30 minutes after mixing), whereas formulations containing 50% and 30% GAX would not be injectable after 30 minutes. As previously described in Example 1, above, compositions containing higher GAX concentrations did not achieve ultimate gel strengths as high as those containing lower GAX concentrations.

Example 4 (Biocompatibility of Crosslinked Collagen Compositions)

An in vivo animal study to evaluate the biocompatibility of various crosslinked collagen formulations was conducted using 32 female Hartley guinea pigs. Each animal received 7 intradermal implants consisting of 0.05 to 0.1 ml each of material according to the schedule shown below.

Site 1  Zyderm ® I Collagen (NX)
Site 2  NX crosslinked with 0.3 wt % DSG-PEG (3800 MW)
Site 3  Zyplast ® Collagen (GAX) crosslinked with 0.3 wt % DSG-PEG (3800 MW)
Site 4  GAX
Site 5  GAX/NX in a 70:30 weight ratio
Site 6  GAX/NX in a 70:30 weight ratio, crosslinked with 0.3 wt % DSG-PEG (3800 MW)
Site 7  Sterile phosphate-buffered saline (PBS) solution (Control)

Groups consisting of 8 animals each were euthanized at 7, 14, 28, and 62 days post-implantation and histology examinations conducted.

Histological evaluation showed that, at day 7, almost all animals had implanted material present within the reticular dermis in all implant sites. In a minority of cases, the implant was localized primarily in the subcutaneous fat, which was slightly more likely to occur in the GAX/DSG-PEG sites than in any of the others. A bolus configuration was the usual pattern in sites receiving GAX, and a more diffuse pattern was present in most sites receiving the other formulations. The implanted material was essentially unchanged in amount, pattern of distribution, or location within the skin between 7 and 14 days, with the exception that, by day 14, no implant could be seen in sites receiving the phosphate-buffered saline solution (PBS) control. By day 28, the amount of the implant appeared smaller in sites receiving NX. Sites receiving the other formulations appeared similar to earlier explant times. By day 62, all formulations showed less implanted material, with GAX formulations persisting most consistently.

A mild to moderate granulomatous response was present in most of the experimental animals at the 7-day time point. The control sites showed virtually no granulomatous response. The granulomatous response was slightly more prominent surrounding the sites receiving NX than any of the other sites, and may have been slightly more pronounced in sites receiving the 70:30 GAX / NX / DSG-PEG group (though the differences were quite small). In general, granulomatous response was slightly less prominent at all implant sites at day 14 than at day 7. At day 28, inflammation at all sites was not significantly different than that seen at day 14. By day 62, inflammation in sites containing residual implanted material was minimal.

At the 7-day time point, ingrowth of fibroblasts was not pronounced in any of the formulation groups, but was seen to a slight degree in the majority of sites receiving NX, and in a small minority of sites receiving the other formulations. The number of animals demonstrating ingrowth of fibroblasts into the implanted material at 14 days showed only a very slight increase over that observed at 7 days. This increase seemed to persist, and perhaps even increase further, by day 28, becoming more common than not by this point in time. By day 62, all remaining implants showed a small degree of fibroblast ingrowth.

Eosinophils were not prominent in any of the animals at day 7, but were present in small amounts in many animals by day 14, and in mild to moderate numbers in the majority of animals by day 14. By day 62, virtually all explants containing residual implanted material with surrounding inflammation exhibited a significant number of eosinophils.

Extensive calcification in two GAX implants and single sites of the 70:30 and 70:30 / DSG-PEG materials was seen at day 62. Calcification had not been observed to any degree at any of the earlier time points. (Calcification of implants is an artifact not generally observed in human subjects.)

The results of the study indicate that all of the materials tested can be considered to be biocompatible. The granulomatous response to all implant materials was mild, and the mild inflammation that was seen at the earlier time points decreased over time and was minimal by day 62. Fibroblast ingrowth was observed in all implant materials by the end of the study.

Example 5 (Biocompatibility of Crosslinked Collagen Compositions)

An in vivo animal study to evaluate the effect of DS-PEG concentration on the biocompatibility of crosslinked collagen formulations was conducted using 54 female Hartley guinea pigs. The biocompatibility of mixtures of Zyplast® and Zyderm® I Collagens, having GAX / NX weight ratios of 80:20, 70:30, and 60:40, and crosslinked using either 0.2, 0.3, or 0.4 percent by weight DSG-PEG (3800 MW), was evaluated. The animals were divided into 6 groups of 9 animals each. Each animal received 6 intradermal implants consisting of 0.05 ml each of material according to the schedule shown below.

Site 1  Zyderm ® I Collagen (NX)
Site 2  Zyplast ® Collagen (GAX)/NX in an 80:20 weight ratio, crosslinked with 0.2, 0.3, or 0.4 wt % DSG-PEG
Site 3  GAX/NX in a 70:30 weight ratio, crosslinked with 0.2, 0.3, or 0.4 wt % DSG-PEG
Site 4  GAX/NX in an 80:20, 70:30, or 60:40 weight ratio
Site 5  GAX
Site 6  GAX/NX in a 60:40 weight ratio, crosslinked with 0.2, 0.3, or 0.4 wt % DSG-PEG As shown above, in order to evaluate various GAX / NX mixtures and various concentrations of DSG-PEG, the formulations implanted at each site varied slightly from animal to animal. Groups consisting of 18 animals each were euthanized at 7, 14, and 30 days post-implantation and histology examinations conducted.

After 7 days, implanted material was found at each explant site, almost always in a diffuse configuration located primarily within the reticular dermis. No implanted material was seen in three sites, two of which had received GAX and one of which had received NX. Some of the explant sites which had received GAX also contained the implanted material in the subcutaneous tissue or around the underlying skeletal muscle, deeper than that observed with most of the other implanted materials. A bolus-like configuration was seen in almost all of the GAX implants, but observed in only a very few cases among the other formulations examined. At 14 days, one explant site which had received NX showed no residual implant. All other explanted tissue contained implanted material, which was found largely in the reticular dermis, but extended into the subcutaneous fat in a majority of sites. In general, after 14 days, the implants retained the diffuse configuration observed at the 7-day timepoint, except in the sites receiving GAX, in which the implants retained their bolus-like configurations. At day 30, implanted material was observable in all explant sites except two NX sites. The remaining implanted material was present mostly within the reticular dennis, with frequent extension into the underlying subcutaneous tissue. In general, the PEG-crosslinked sites showed a slight trend toward less diffuse extension of the implanted material and retention of a more bolus-like configuration.

At the 7-day time point, animals receiving NX showed minimal to mild inflammation surrounding the implanted material. The GAX / NX 80:20 / 0.2% DSG-PEG group showed a moderate inflammatory infiltrate in 5 of 6 animals examined. The same formulation with 0.3% DSG-PEG showed a very similar response. However, when the same formulation was crosslinked with 0.4% DSG-PEG, the inflammatory infiltrate was more variable from animal to animal, and very intense in several cases. The formulations GAX / NX 70:30 with 0.2, 0.3, and 0.4% DSG-PEG also showed a moderately intense inflammatory infiltrate in most animals. The explants that contained GAX / NX 80:20 showed only mild inflammation or, in some cases, virtually none. Reactions to the GAX / NX 70:30 formulation were more variable, ranging from nonexistent to intense inflammation in one case. In the 60:40 GAX / NX group, the inflammatory response was mild to nonexistent in 5 of the 6 animals, but intense in the sixth animal. The inflammatory response to GAX varied from nonexistent to moderate, with most explant sites having only a mild lymphohistiocytic host response.

In general, the degree of inflammatory infiltrate decreased for all formulations with passage of time. The NX sites maintained a relatively low degree of inflammation throughout. Sites containing mixtures of GAX and NX crosslinked with DSG-PEG had more inflammation throughout and, at both the 7- and 30-day time points, inflammation appeared to be slightly more intense with higher concentrations of DSG-PEG.

Fibrosis surrounding the implanted material was essentially absent at the 7-day time point. A small focus of fibrosis was seen in a single site, which had a moderate degree of surrounding inflammation, in one animal in the GAX group. Fibrosis was not seen around any of the implants at the 14- and 30-day time points.

At the 7-day time point, fibroblast ingrowth was seen in the majority of explants containing NX, but was rarely seen in explants containing any of the other formulations. By the 14-day time point, mild fibroblast ingrowth was seen in the majority of implants. Fibroblast ingrowth reached a moderate level in a single implant containing GAX, which is surprising in that most of the GAX implants did not display any fibroblast ingrowth. In fact, the GAX implants were the only formulation that did not display fibroblast ingrowth to some degree in most cases. By 30 days, the majority of implants showed fibroblast ingrowth. Eleven of 18 sites containing NX had a mild degree of ingrowth, with the other 7 demonstrating very little ingrowth. Only 8 of 18 sites containing the GAX / NX 80:20/ DSG-PEG formulation had mild ingrowth, with the other 10 sites showing no ingrowth. This did not appear to vary with concentration of DSG-PEG. Thirteen of 18 sites containing the GAX / NX 70:30 / DSG-PEG formulation showed mild fibroblast ingrowth, with the other 5 sites showing no fibroblast ingrowth. Fourteen sites containing GAX / NX 80:20 showed a mild degree of fibroblast ingrowth, with the remaining 4 sites showing no ingrowth. The majority of sites containing GAX demonstrated a mild amount of fibroblast ingrowth, with moderate ingrowth observed at 2 sites. Ten of 18 sites containing GAX / NX 60:40 / DSG-PEG showed mild fibroblast ingrowth, with 1 site demonstrating moderate ingrowth, and the other 7 showing no significant ingrowth. In general, the degree of fibroblast ingrowth did not appear to vary with DSG-PEG concentration.

At the 7-day time point, eosinophils were detected to a mild degree in a significant number of explants of all formulations tested. In rare cases, moderate numbers of eosinophils were present. At 7 days, eosinophils were most likely to be present in explants containing formulations of GAX / NX 80:20 and 70:30, regardless of the DSG-PEG concentration. At 14 days, the majority of implant sites contained scattered eosinophils, which were present in moderate numbers in about one-third of the explants examined. There was no apparent difference in degree of tissue eosinophilia between formulations. Eosinophils were present in mild amounts in the majority of explant sites at 30 days. Several sites demonstrated moderate or abundant numbers of eosinophils, which did not appear to be associated with specific implant materials.

At the 7-day time point, abundant neutrophils, occasionally forming abscesses, were seen in rare cases. In a single case, the intense inflammation showed surrounding calcification. The appearance of neutrophils was most common in formulation groups containing GAX and NX in various proportions, but was also seen in the NX group. At the 14-day time point, a single site receiving GAX showed calcification. Calcification was present in a minority of implants by 30 days, most commonly being observed in GAX and GAX / NX / DSG-PEG implants, with no differences observed between formulations containing varying amounts of the three components.

These results demonstrate that implants consisting of GAX / NX mixtures injected into the dermis and crosslinked in situ with DSG-PEG are biocompatible. In general, these implant materials showed a slightly greater inflammatory response than implants containing NX alone and greater tissue ingrowth than implants containing GAX alone. Inflammation appeared to be slightly increased in GAX / NX implants containing the highest percentage (0.4% by weight) of DSG-PEG. Sites containing PEG-crosslinked collagen formulations generally showed less diffuse extension of the implanted material and retention of a more bolus-like configuration.

Example 7 (Method of Preparing and Administering Crosslinked Collagen Compositions for Soft Tissue Augmentation)

A physician opens a kit containing the following components: one 1-cc syringe containing 1 ml of a mixture of Zyderm® and Zyplast® Collagens in a 70:30 weight ratio; one 3-cc syringe containing 3 mg of sterile, dry, difunctionally activated SG-PEG (DSG-PEG, MW 3800); one three-way stopcock; and several 30-gauge needles. The physician connects the syringe containing the collagen mixture with the syringe containing the dry DSG-PEG by means of the three-way stopcock. She then mixes the collagen and DSG-PEG back and forth between the syringes, employing at least 30 passes of material between the syringes. She then transfers all of the material back into the 1-cc syringe (which formerly contained just the collagen mixture), detaches the empty 3-cc syringe from the stopcock, then attaches one of the 30-gauge needles to the full 1-cc syringe.

After attaching the needle to the syringe, the physician injects the collagen and DSG-PEG subcutaneously, using multiple serial punctures, to soft tissue sites in need of augmentation, such as acne scars and wrinkles. Following injection, the doctor gently massages the material beneath the patient's skin to achieve an even distribution of the implanted collagen within the dermis in order to avoid lumping or beading of the material. Treatment of the patient is completed within approximately 40 minutes of mixing the collagen mixture with the DSG-PEG.

What is claimed is:

1. An injectable collagen composition comprising particulate crosslinked collagen, noncrosslinked collagen, and a multifunctionally activated synthetic hydrophilic polymer having two or more functional groups capable of reacting with primary amino groups on collagen molecules to form a crosslinked matrix between the crosslinked collagen and the noncrosslinked collagen.

2. The composition of claim 1, wherein the particulate crosslinked collagen is crosslinked using a method selected from the group consisting of: heat, irradiation, and chemical crosslinking agents.

3. The composition of claim 2, wherein the particulate crosslinked collagen is crosslinked using a chemical crosslinking agent selected from the group consisting of: aldheydes, divinyl sulfone, epoxides, carbodiimides, imidazole, synthetic hydrophilic polymers, and mixtures thereof.

4. The composition of claim 3, wherein the particulate crosslinked collagen is glutaraldehyde-crosslinked collagen.

5. The composition of claim 1, wherein the particulate crosslinked collagen comprises between about 25% and 95% by weight of the composition.

6. The composition of claim 1, wherein the particulate crosslinked collagen comprises between 60% to about 80% by weight of the composition.

7. The composition of claim 1, wherein the non-crosslinked collagen is atelopeptide collagen.

8. The composition of claim 1, wherein the non-crosslinked collagen is fibrillar collagen.

9. The composition of claim 8, wherein the non-crosslinked collagen comprises between about 5% to about 75% by weight of the composition.

10. The composition of claim 9, wherein the non-crosslinked collagen comprises between about 20% to about 40% by weight of the composition.

11. The composition of claim 1, wherein the multifunctionally activated synthetic hydrophilic polymer is selected from the group consisting of multifunctionally activated derivatives of: polyethylene glycol, polyoxyethylene, polymethylene glycol, polytrimethylene glycols, polyvinylpyrrolidones, and polyoxyethylene-polyoxypropylene block polymers and copolymers.

12. The composition of claim 11, wherein the multifunctionally activated synthetic hydrophilic polymer is a multifunctionally activated derivative of polyethylene glycol.

13. The composition of claim 12, wherein the multifunctionally activated polyethylene glycol derivative is selected from the group consisting of; polyethylene glycol succinimidyl glutarate, succinimidyl, succinimidyl succinamide, and succinimidyl carbonate.

* * * * *